United States Patent
Gupta et al.

(10) Patent No.: US 10,280,445 B2
(45) Date of Patent: May 7, 2019

(54) CHROMOGEN LAYERING FOR COLOR GENERATION

(71) Applicants: Bipin Gupta, Pleasanton, CA (US); Marc Key, Ojai, CA (US)

(72) Inventors: Bipin Gupta, Pleasanton, CA (US); Marc Key, Ojai, CA (US)

(73) Assignees: Diagnostic BioSystems, Pleasanton, CA (US); Marc Key, Ojai, CA (US)

( * ) Notice: Subject to any disclaimer, the term of this patent is extended or adjusted under 35 U.S.C. 154(b) by 0 days.

(21) Appl. No.: 15/650,940

(22) Filed: Jul. 16, 2017

(65) Prior Publication Data
US 2018/0258463 A1     Sep. 13, 2018

Related U.S. Application Data

(60) Provisional application No. 62/469,399, filed on Mar. 9, 2017.

(51) Int. Cl.
| C12Q 1/28 | (2006.01) |
| C12Q 1/42 | (2006.01) |
| G01N 1/30 | (2006.01) |
| G01N 33/53 | (2006.01) |

(52) U.S. Cl.
CPC ............... *C12Q 1/28* (2013.01); *G01N 33/53* (2013.01); *C12Q 1/42* (2013.01); *C12Q 2326/40* (2013.01); *G01N 1/30* (2013.01); *G01N 2001/302* (2013.01); *G01N 2458/00* (2013.01)

(58) Field of Classification Search
CPC ........ C12Q 1/28; C12Q 1/42; C12Q 2326/40; G01N 2001/302; G01N 1/30; G01N 33/53; G01N 2458/00
See application file for complete search history.

(56) References Cited

U.S. PATENT DOCUMENTS
| 8,658,361 B2 | 2/2014 | Wu et al. |
| 2013/0260379 A1 | 10/2013 | Alexander et al. |
| 2017/0175178 A1 | 6/2017 | Lohse et al. |

FOREIGN PATENT DOCUMENTS
| WO | 2011133625 A1 | 10/2011 |
| WO | WO-2011133625 A1 * | 10/2011 ........... C12Q 1/6841 |

OTHER PUBLICATIONS

Van der Loos et al. An Immunoenzyme Triple-staining Method Using Both Polyclonal and Monoclonal Antibodies from the Same Species. Application of Combined Direct, Indirect, and Avidin-Biotin Complex (ABC) Technique. Journal of Histochemistry and Cytochemistry (1987), v35(11), p. 1199-1204. (Year: 1987).*

(Continued)

*Primary Examiner* — Sean C. Barron
(74) *Attorney, Agent, or Firm* — Patentfile, LLC; Bradley C. Fach; Steven R. Kick

(57) ABSTRACT

The present disclosure relates methods of chromogen layering, wherein a first chromogen and a first stain (color) are produced on a sample, specific for a first analyte, followed by a second chromogen and a second stain (color) being produced on the same sample, specific for a second analyte. In addition, if desired, by overlaying the second stain on top of the first stain, a unique third color is produced that is specific for a third analyte. Therefore, the distribution of different colors throughout the sample could be used to identify at least two or more analytes simultaneously within a single sample.

9 Claims, 12 Drawing Sheets

(56) References Cited

OTHER PUBLICATIONS

Van der Loos Chromogens in Multiple Immunohistochemical Staining Used for Visual Assessment and Spectral Imaging: The Colorful Future. The J Histotechnol (2010), v33(1), v31-40. (Year: 2010).*
Lauter et al. Two-color fluorescent in situ hybridization in the embryonic zebrafish brain using differential detection systems. Developmental Biology (2011), v11(43), 11 pages. (Year: 2011).*
Stack et al. Multiplexed immunohistochemistry, imaging, and quantitation: A review, with an assessment of Tyramide signal amplification, multispectral imaging and multiplex analysis. Methods (2014), v70, p. 46-58. (Year: 2014).*
Dixon et al. Recent developments in multiplexing techniques for immunohistochemistry. (Expert Rev Mol Diagn. (2015), v15(9), 28 page author manuscript. (Year: 2015).*
Nakata et al. Chromogen-based Immunohistochemical Method for Elucidation of the Coexpression of Two Antigens Using Antibodies from the Same Species. Journal of Histochemistry & Cytochemistry (2012), v60(8), p. 611-619. (Year: 2012).*
Chen X, Cho DB, Yang PC. Double staining immunohistochemistry. N Am J Med Sci 2(5): 241-245, 2010.
Ghandour MS, Langley OK, Vincendon G, Gombos G, Double labeling immunohistochemical technique provides evidence of specificity of glial cell markers. J Histochem Cytochem 27: 1634-1637, 1979.
Tischler AS. Triple immunohistochemical staining for bromodeoxyuridine and catecholamine biosynthetic enzymes using microwave antigen retrieval. J Histochem Cytochem 43: 1-4, 1995.
Lan HY, Mu W, Nikolic-Paterson, Dj, Atkins RC. A novel, simple reliable, and sensitive method for multiple immunoenzyme staining: Use of microwave oven heating to block antibody cressreactivity and retrieve antigens. J Histochem Cytochem 43: 97-102, 1995.
Hunyady B, Krempels K, Harta G, Mezey E, Immunohistochemical signal amplification by catalyzed reporter deposition and its application in doube immunostaining. J Histochem Cytochem 44: 1353-1362, 1996.
Pham N-A, Morrison A, Schwock J, Aviel-Ronen S, Iakovlev V, Tsao M-S, Ho J, Hedley DW. Quantitative image analysis of immunenistochemical stains using a CMYK color model. Diag Pathol 2007: 2(8) p. 1-10.
Nakata T, Suzuki N. Chromogen-based lmmunohislochernical Method for Elucidation of the Coexpression of Two Antigens Using Antibodies from the Same Species. J Histochem Cytochem 60(8) 611-619, 2012.
Schutz A. Tannapfel A, Wittekind C. Comparison of different double immunostaining protocols for paraffin embedded liver tissue. An Cell Path 18:227-233, 1999.
Fu R, Ma X, Bian Z, Ma J. Digital separation of diaminobenzidine-stained tissues via an automatic color-filtering for immunohistochemical quantification. Biomed Opt Exp 6: 544-558, 2015.
Wahlby C, Erlandsson F, Bengtsson E, Zetterberg A. Sequential immunofluorescence staining and image analysis for detection of large numbers of antigens in individual cell nuclei. Cytometry 47: 32-41, 2002.
Pirici D, Mogoanta L. Kumar-Singh S, Pirici I, Margaritescu C, Simionescu C, Stanescu R. Antibody elution method for multiple immunohistochemistry on primary antibodies raised in the same species and of the same subtype. J Histochm Cytochem 57: 567-575, 2009.
Tao Q, Srivastava G, Loke SL, Chan Yet, Ho FCS. Improved double immunohtstochemical staining method for cryostat and paraffin wax sections, combining alkaline phosphatase anti-alkaline phosphatase and indirect immunofluorescence. J Clin Pathol 47. 597-600, 1994.
Van Der Loos CM. Multiple immunoenzyme staining. Methods aid visualizations for the observation with spectral imaging. J Histochem Cytochem 56: 313-328, 2008.
NPL—Cite No. 1—Laakso, M; Tanner, M; Isola, J; "Dual-colour chromogenic in situ hybridization for testing of HER-2 oncogene amplification in archival breast tumours" Journal of Pathology, 210, 3-9, 2006 (Year: 2006).

* cited by examiner

CHROMOGEN LAYERING FOR COLOR GENERATION

CROSS REFERENCE TO RELATED APPLICATION

This application claims the benefit of U.S. Provisional Application No. 62/469,399, filed Mar. 9, 2017, entitled CHROMOGEN LAYERING FOR COLOR GENERATION, which is herein incorporated by reference in its entirety for all purposes.

INCORPORATION BY REFERENCE

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

INTRODUCTION

A biological specimen on a microscope slide may be stained by various methods to reveal, by microscopic analysis, molecular and histologic structures (such as analytes) within the specimen. This disclosure relates to a chromogen layering method that is useful to generate new colors for staining biological samples.

BACKGROUND OF THE DISCLOSURE

A biological sample, such as a tissue biopsy is obtained for analysis. The analysis will be a molecular analysis to determine if a specific analyte is present within the sample. The presence or absence of an analyte is frequently used to determine a disease state, such as cancer. For successful analysis, the tissue is processed by fixation, embedding, and sectioning onto a microscope slide. In preparation for staining, the tissue is deparaffinzed, rehydrated, and treated by target retrieval to render the presumed analyte susceptible to staining. The samples are then stained by either ISH or IHC to render the presumed analyte colored and visible when examined under the microscope. Thus, the analyte is either present (colored) or absent (not colored), and the disease state of the tissue is then determined.

What is needed is a method for not only determining the presence or absence of a single analyte, but also the presence or absence of multiple analytes. It would be useful to have a method of chromogen layering, wherein a first chromogen and a first stain (color) are produced on a sample, specific for a first analyte, followed by a second chromogen and a second stain (color) being produced on the same sample, specific for a second analyte. In addition, if desired, by overlaying the second stain on top of the first stain, a unique third color is produced that is specific for a third analyte. Therefore, the distribution of different colors throughout the sample could be used to identify at least two or more analytes simultaneously within a single sample.

SUMMARY OF THE DISCLOSURE

Disclosed herein are methods of chromogen layering, which includes staining biological samples using the methods of immunohistochemistry or in situ hybridization in such a way that multiple analytes can be identified in a single specimen.

Disclosed herein are methods of staining one section of a biological specimen for one or more different analytes, comprising: obtaining a section of a biological specimen; contacting the section with a first antibody directed towards a first analyte, wherein the first antibody is labeled with a first marker or wherein the first antibody becomes labeled with a first marker by means of a linking step; contacting the section with a first chromogen that reacts with the first marker to generate a first color; contacting the section with a second antibody directed towards a second analyte, wherein the second antibody is labeled with a second marker or where the second antibody becomes labeled with a second marker by means of a linking step; contacting the section with a second chromogen that reacts with the second marker to generate a second color; and observing the presence or absence of a first, second, or a third color wherein the third color is a result of overlapping of the first and second colors. In one embodiment, the first antibody and the second antibody are the same. In another embodiment, the first antibody and the second antibody are different. In one embodiment, the first marker and the second marker are the same. In another embodiment, the first marker and the second marker are different. In other embodiments of the disclosed methods, the first chromogen comprises 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue, and the second chromogen comprises a different chromogen than the first chromogen, chosen from 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue. In other embodiments, a) the first chromogen's color is blue, the second chromogen's color is yellow, and the third color is green; or b) the first chromogen's color is yellow, the second chromogen's color is blue, and the third color is green; or c) the first chromogen's color is blue, the second chromogen's color is red, and the third color is purple; or d) the first chromogen's color is red, the second chromogen's color is blue, and the third color is purple; or e) the first chromogen's color is yellow, the second chromogen's color is red, and the third color is orange; or f) the first chromogen's color is red, the second chromogen's color is yellow, and the third color is orange.

In one embodiment, the first marker or the second marker is an enzyme. In other embodiments, a) the enzyme is a peroxidase, horse radish peroxidase, a phosphatase, alkaline phosphatase, beta-galactosidase, or any enzyme that reacts with a colorless compound to create a colored chromogen capable of staining the biological specimen. In other embodiments of the disclosed methods, the observation is by a person's eyes or the observation is a digital image.

Also disclosed are methods of staining one section of a biological specimen for one or more different analytes, comprising: obtaining a section of a biological specimen; contacting the section with a first probe directed towards a first analyte, wherein the first probe is labeled with a first marker or wherein the first probe becomes labeled with a first marker by means of a linking step; contacting the section with a first chromogen that reacts with the first marker to generate a first color; contacting the section with a second probe directed towards a second analyte, wherein the second probe is labeled with a second marker or where the second probe becomes labeled with a second marker by means of a linking step; contacting the section with a second chromogen that reacts with the second marker to generate a second color; and observing the presence or absence of a first, second, or a third color wherein the third color is a result of overlapping of the first and second colors. In one embodiment, the first antibody and the second probe are the same. In another embodiment, the first antibody and the second probe are different. In yet another embodiment, the first marker and the second marker are the same. In another embodiment, the first marker and the second marker are different. In other embodiments of the disclosed methods, the first chromogen comprises 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue, and the second chromogen comprises a different chromogen than the first chromogen, chosen from 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue. In other embodiments, a) the first chromogen's color is blue, the second chromogen's color is yellow, and the third color is green; or b) the first chromogen's color is yellow, the second chromogen's color is blue, and the third color is green; or c) the first chromogen's color is blue, the second chromogen's color is red, and the third color is purple; or d) the first chromogen's color is red, the second chromogen's color is blue, and the third color is purple; or e) the first chromogen's color is yellow, the second chromogen's color is red, and the third color is orange; or f) the first chromogen's color is red, the second chromogen's color is yellow, and the third color is orange. In another embodiment of the disclosed methods, the first marker or the second marker is an enzyme. In yet embodiments, the enzyme is a peroxidase, horse radish peroxidase, a phosphatase, alkaline phosphatase, beta-galactosidase, or any enzyme that reacts with a colorless compound to create a colored chromogen capable of staining the biological specimen. In other embodiments, the observation is by a person's eyes or the observation is a digital image.

Also disclosed are biological specimens stained for three different analytes, wherein the first analyte is stained a first color and the second analyte is stained a second color, and a third analyte is identified by a third color that is not the first color or the second color. In some embodiments, the first color is blue, the second color is yellow, and the third color is green; the first color is yellow, the second color is blue, and the third color is green; the first color is blue, the second color is red, and the third color is purple; the first color is red, the second color is blue, and the third color is purple; the first color is yellow, the second color is red, and the third color is orange; or the first color is red, the second color is yellow, and the third color is orange.

Also disclosed are methods of staining one section of a biological specimen for one or more different analytes, comprising: obtaining a section of a biological specimen; contacting the section with a first antibody directed towards a first analyte, wherein the first antibody is labeled with a first marker or wherein the first antibody becomes labeled with a first marker by means of a linking step; contacting the section with a first chromogen that reacts with the first marker to generate a first color; contacting the section with a second chromogen that reacts with the first marker to generate a second color; and observing the presence or absence of a first and second colors that together form a third color wherein the third color is a result of overlapping of the first and second colors. In other embodiments of the disclosed methods, the first chromogen comprises 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue, and the second chromogen comprises a different chromogen than the first chromogen, chosen from 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, or naphthol-blue.

BRIEF DESCRIPTION OF THE DRAWINGS

These and other features, aspects, and advantages of the present disclosure will become better understood with regard to the following description, appended claims and accompanying figures where:

DETAILED DESCRIPTION OF THE DISCLOSURE

Figure 1:
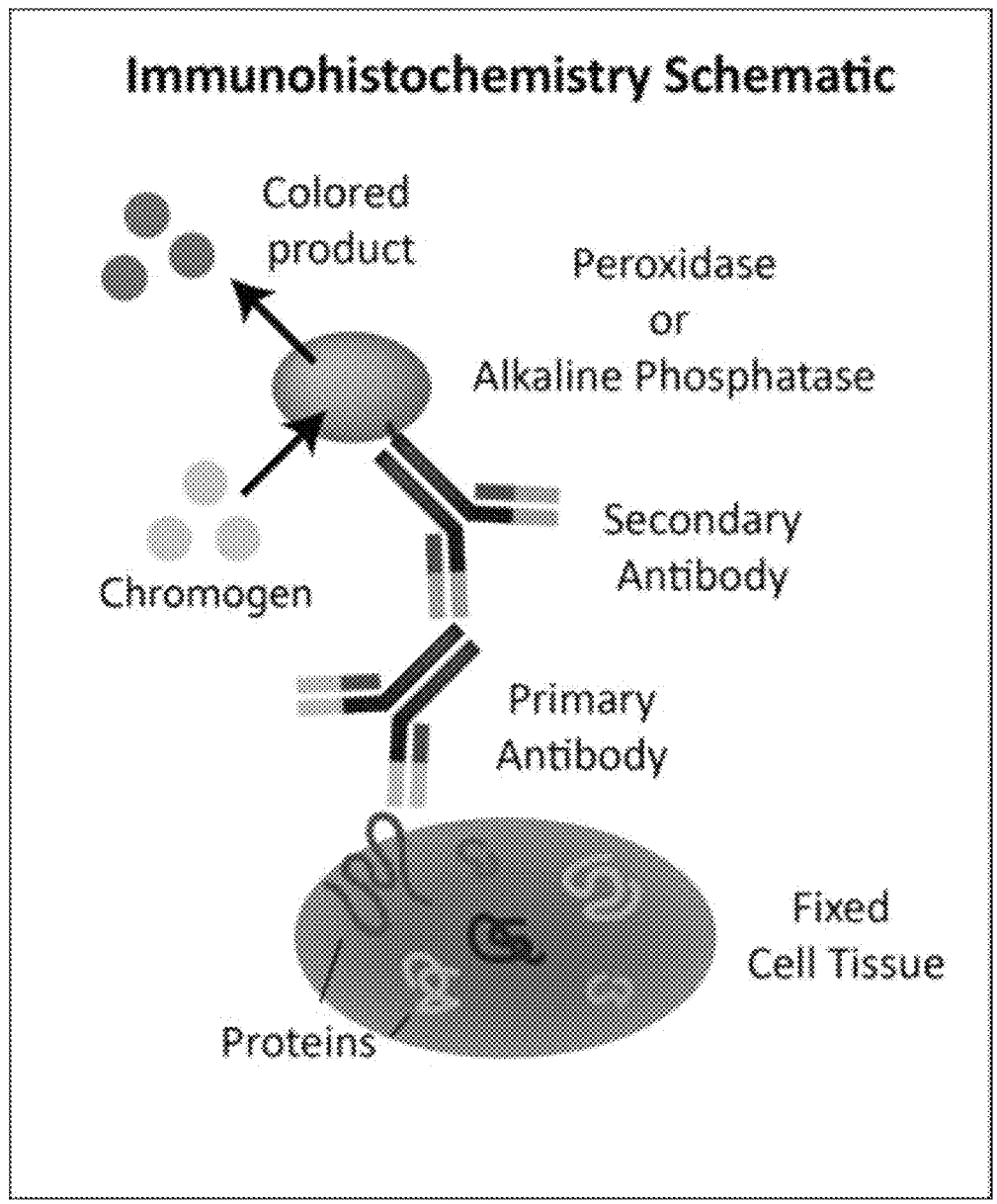
FIG. 1 shows a diagram of a standard immunohistochemistry (IHC) method: 1) primary antibody, 2) secondary antibody containing 3) an enzyme (peroxidase or alkaline phosphatase), and 4) a colored layer (chromogen).

The following detailed description is provided to aid those skilled in the art in practicing the present disclosure. Even so, this detailed description should not be construed to unduly limit the present invention as modifications and variations in the embodiments discussed herein can be made by those of ordinary skill in the art without departing from the spirit or scope of the present inventive discovery.

As used in this disclosure and the appended claims, the singular forms "a", "an" and "the" include a plural reference unless the context clearly dictates otherwise. As used in this disclosure and the appended claims, the term "or" can be singular or inclusive. For example, A or B, can be A and B.

For example, "an antibody" can mean one or more antibodies, for example, a cocktail of two antibodies.

Ranges

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

About

The term "about" generally refers to plus or minus 10% of the indicated number. For example, "about 10%" may indicate a range of 9% to 11%, and "about 1" may mean from 0.9-1.1.

Specimen/Sample

The words "specimen" and "sample" are used interchangeably throughout the disclosure. A specimen can be a biological specimen. A specimen can be one or more cells, a mixture of different types of cells, or a population of cells. A specimen can comprise eukaryotic or prokaryotic cells or a mixture of both. A specimen, such as a group of cells, can be grown directly on a surface suited for cell culture (e.g. a tissue culture dish) or loose cells can be applied to a surface, for example, a microscope slide. A specimen can be a tissue sample or a portion or slice of a tissue sample. A specimen can be embedded in a matrix, such as paraffin, or may be freshly frozen after collection from a mammal (e.g. human or animal).

Analytes

The terms "analyte", "target" and the phrase "target analyte" can be used interchangeably throughout the disclosure.

An analyte is any substance whose chemical constituents are being identified, measured, or analyzed. An analyte can be located in a cell or a tissue. An analyte can be located within various cells or structures distributed throughout the tissue. Exemplary analytes are nucleic acid analytes, or antigen analytes, such as proteins. An analyte can be, for example, RNA, DNA, or any molecule found in a cell. An analyte can be, for example, an organic molecule such as a sugar, starch, lipid, fatty acid, or amino acid. An analyte can also be, for example, a pathogen such as a bacterium, virus, fungus, yeast, or eukaryotic parasite. One or more analytes can be detected using the disclosed methods.

Staining

Staining is a technique used in microscopic analysis to enhance contrast in the microscopic image. Stains and dyes can be chemical compounds or biological molecules. A stain or dye can be tagged, conjugated to, or be labeled with another chemical compound.

Stains and dyes are often used to highlight structures in biological tissue samples to define and examine particular tissue structures, cell populations, or organelles within individual cells. Stains and dyes may also be specific to particular DNA, proteins, lipids, or carbohydrates present in the specimen, and help to determine the presence or absence, or the quantity of the particular species of interest.

The term "staining" refers to a formation of specific binding interaction between the stains or the dyes to the species of interest. For example, a staining may occur when a biomarker, such as an antibody, specifically binds to a protein or an antigen; when a nucleic acid binds to a DNA or RNA sequence; or when a chemical compound that specifically recognizes the nucleus of a cell producing a visible color upon the subsequent contact of a substrate.

Dyes/Stains

The terms "dye" and "stain" can be used interchangeably throughout the disclosure. A dye/stain can also be a chromogen.

Dyes demonstrate an affinity for molecules or organisms within cells and tissues. For example, a dye (stain) can be specific to connective tissue, erythrocytes, mitochondria, nucleic acids, collagen, reticulum, muscle, plasma, nuclei, bacteria, nerve cells, liver cells, cell walls, pituitary cells, reticulum, bone, cartilage, pancreatic cells, marrow cells, cytoplasm, parasites, keratin, or any portion or combination of any of the above.

The affinity of dyes for elements that are present in a cell or tissue is affected by several factors: the structure of the dye molecule; the shape of the dye molecule; the charge distribution of the dye; and solvent characteristics. Stains can be used on fixed, or non-living cells.

Chromogen

A chromogen is a substance capable of conversion into a pigment or dye (a stain). A chromogen begins as a colorless compound that is converted to a colored compound during the staining process by an enzymatic reaction. A chromogen can be mixed with a substrate. The chromogen/substrate mixture is then converted by an enzymatic reaction to a colored compound.

Typically, the enzymes horseradish peroxidase (HRP) or alkaline phosphatase (AP) are used with an appropriate chromogen/substrate to produce a reaction product that can generally be visualized using light microscopy. For example, HRP (enzyme) can be used with a chromogen and a substrate (hydrogen peroxide). Alternatively, AP (enzyme) can be used with a chromogen and a substrate (naphthol-phosphate). Other peroxidases and phosphatases can also be used. Any chromogen that uses either Horseradish Peroxidase (HRP), Peroxidase, or Alkaline Phosphatase (AP), or phosphatase as an enzyme label can be used in the disclosed chromogen layering methods.

Exemplary chromogens are: 3,3',5,5', tetramethylbenzidine (TMB); 3,3'-diaminobenzidine (DAB); Fast Red TR; New Fuchsin; PermaBlue; PermaGreen; PermaYellow; PermaBlack; PermaRed; Benzidine; 3-Amino-9-ethylcarbazole (AEC); Variamine Blue; Fast Blue BB: Basic Fuchsin; New Fucsin. Pararosanaline: Indoxyl phosphates; 6-Chloro-3-indoxyl phosphate (CIP); 5-Bromo-4-chloro-3-indoxyl phosphate (BCIP); 3-indoxyl phosphate; a tetrazolium, Nitro blue tetrazolium (NBT); Tetranitro blue tetrazolium (TNBT); Iodonitro tetrazolium (INT); HRP-Red; HRP-Blue (generic name is tetramethylbenzidine); FastRed/Napthol Phosphate; FastBlue/Napthol Phosphate; or Fast Red.

Stable DAB Plus, (generic name is diaminobenzidine), Diagnostic BioSystems Catalog No. K047, color is brown, as described in Graham, R. C. and Karnovsky, J. J., J. Histochem. Cytochem., 14, 291 (1966).

PermaYellow/HRP, (generic name is HRP-Yellow), Diagnostic BioSystems Catalog No. K060, color is yellow.

PermaRed/HRP, (generic name is Naphthol-Red), Diagnostic BioSystems Catalog No. K075, color is red, as described in Elias, J. M. Am J Clin Pathol. 1980 June; 73(6):797-9.

PermaBlue/HRP, (generic name is Napthol-Blue), Diagnostic BioSystems Catalog No. K063, color is blue, as described in Batteiger, B., Journal of Immunological Methods, 55 (1982) 297-307.

HRP-Blue, (generic name is tetramethylbenzidine), color is blue, as described in Weinburg R. J. and VanEck, S. L. J. Histochem. Cytochem., 39: 1143-1148 (1991).

AP-Red, (generic name is Fast Red), color is red, as described in Speel, E. J., et al. J. Histochem. Cytochem. 40: 1299-1308, 1992.

Contacting

Contacting, for example, a specimen with a stain, dye, or chromogen, can be by submerging, incubating, applying, soaking, pouring, or layering the specimen with the stain, dye, or chromogen.

Contacting a specimen with a stain, dye, or chromogen, as disclosed herein, can be for any period of time sufficient to stain the specimen. For example, about 1 to 5 minutes, or 5 minutes to 20 minutes, or 20 minutes or more, up to 24 hours.

Contacting a specimen with a cocktail of one or more antibodies, as disclosed herein, can be for any period of time sufficient for the one or more antibodies to bind to an analyte(s) present in the specimen. For example, about 1 to 5 minutes, or 5 minutes to 20 minutes, or 20 minutes or more.

Contacting a specimen with one or more probes, as disclosed herein, can be for any period of time sufficient for the one or more probes to bind to an analyte(s) present in the specimen. For example, about 1 to 5 minutes, or 5 minutes to 20 minutes, or 20 minutes or more.

Rinsing

After staining, a specimen can be rinsed to wash the specimen in preparation for the next stain. A typical rinse solution is a buffer, such as 0.1M phosphate buffer or 0.05M Tris buffer, at a pH of about 7 to about 8.

Microscopic Analysis

The term "microscopic analysis" refers to techniques that require a microscope, an instrument or a system that are capable of acquiring data and/or images for analysis. It may be a stand-alone bright-field or fluorescent microscope, a cell imager, a spectrometer, or a manual or automated slide stainer and scanner.

Immunohistochemistry Assays

The biological specimens can be used in immunological methods, such as immunohistochemistry assays (IHC) and immunocytochemistry assays (ICC). The biological specimens can also be used for in situ hybridization assays (ISH), fluorescent in situ hybridization (FISH) assays, and enzyme-linked immunosorbent assays.

Exemplary Sample Preparation

Biological samples of cells and/or tissues are obtained for purposes of analyzing the biological constituents (analytes) that comprise the sample. Sample analysis may be performed by methods of immunohistochemistry (ICH) for analyzing protein components (analytes), or in situ hybridization (ISH) for analyzing nucleic acid components (analytes). Prior to the analysis, the sample must be prepared by appropriate methods. For example, a tissue biopsy is removed from a patient and processed by the following exemplary steps:

1. Fixation: Tissue is fixed to stop all metabolic activity and to preserve the molecular structure of the tissue. A common fixative for this purpose includes aqueous solutions of formalin.

2. Embedding: The tissue is embedded in solid paraffin to provide a firm surrounding matrix. Embedding is the process of infiltrating paraffin into, and around, the biological sample. First the water is removed by dehydration, for example in alcohol, next the alcohol is removed and replaced with a solvent that is miscible with paraffin, such as xylene, toluene, or other hydrocarbon solvent. The tissue thus prepared is then infiltrated with melted paraffin at a temperature of around 60 C, or at a temperature to keep the paraffin in a melted state. After infiltration, the biological samples are cooled, and the paraffin solidifies to create a solid matrix surrounding the sample.

3. Sectioning:

The sample can now be easily cut into thin sections by using a microtome or similar cutting device. The thin paraffin sections, containing the tissue, are usually cut with a thickness of about 4 u. Each section can then be placed upon a microscope slide where it will attach (adhere) by means of electrostatic charges between the tissue section and the slide.

The prepared slides containing paraffin are further processed to remove the paraffin in a process call deparaffinization. Slides for deparaffinization are treated with a paraffin solvent, such as xylene, toluene, or similar hydrocarbon solvent, and the paraffin is dissolved. The next step involves removing the paraffin solvent, and replacing it with alcohol. Because alcohol is miscible with water the slides can now be placed into an aqueous buffer bath for rehydration.

After rehydration, the slides with the attached tissue samples are subjected to physical or chemical treatment to release (retrieve) the analytes (for example, antigens) and make them accessible for subsequent staining.

Alternative Sample Preparation

In addition to formalin, mentioned above, there are several other fixatives that can be used, such as alcohols, (methanol and ethanol), acetone, glutaraldehye, and combinations thereof.

There are also embedding methods that do not include paraffin. One such method is to freeze the tissue sample into a solid block of ice. This renders the sample sufficiently rigid that it can be sectioned into thin slices using a cryostat instrument. Tissues prepared in this manner avoid the paraffin-embedding process as well as the deparaffinization and rehydration processes.

In addition, target (analyte) retrieval can be performed in various different ways. Typically, the rehydrated microscope slides, containing tissues, are submerged into a chemical solution and then subjected to heat at about 100 C. This process of heat-induced target retrieval is designed to render the target molecules susceptible to staining methods. In some instances, it is possible to retrieve targets by using enzymatic methods rather than chemical and physical methods. In this method, the microscope slides containing the sample are exposed to proteolytic enzymes which act to partially digest the tissue and render the analytes accessible to staining. Such proteolytic enzymes may include, for example, pepsin, trypsin, proteinase K, protease XXIV, chymotrypsin, or ficin.

Exemplary Staining of Biological Samples

The prepared biological samples are then stained in a manner to produce a colored stain on the tissue that corresponds to the analyte under evaluation. Two common staining methods are in situ hybridization (ISH) for evaluation of nucleic acids analytes and immunohistochemistry (IHC) for evaluation of antigen analytes, such as proteins. It is typical that the analyte will be located within various cells or structures distributed throughout the tissue. In some instances, it is desirable to stain more than one analyte within a sample such that each analyte is stained a different color.

Disclosed herein are methods of staining a sample, whereby each of the analytes under investigation are stained in a different color. This allows the investigator to view the different colors under the microscope and to quantify each separate analyte based upon the color assigned to each analyte. The use of the disclosed methods in regard to ISH and IHC are described further below.

In the ISH method the target analyte is a nucleic acid usually either an RNA or DNA target. In the first step the sample is contacted with a probe that will specifically recognize and bind to its target. Probes are small lengths of nucleic acids that have been engineered to contain a series of bases that are complementary to the target analyte. Since complementary strands of nucleic acids will pair together, the probe will specifically bind to its complementary target nucleic acid. As an example, an investigator may wish to determine whether a particular gene (target analyte) is present or absent in a sample. If the gene sequence of the target analyte is known, it is then possible to manufacture a probe with a complementary nucleic acid sequence. If the target analyte is present, then the probe will bind to the target. If the target analyte is absent then no binding will occur. The next step is to detect whether or not a binding event has occurred. Typically, the probe will be produced to include a detectable marker. For example, this detectable marker could be an enzyme. If a binding event has occurred then the enzyme will be present at the binding site. If no binding event has occurred then the enzyme will not be present. In one example the enzyme could be Horseradish Peroxidase (HRP), although other enzymes can be used.

Next, the presence or absence of the HRP enzyme is evaluated. The HRP enzyme reacts with various chromogenic compounds to produce a colored-reaction product. The colored-reaction product then stains the tissue at the site of HRP binding. When the tissue is viewed microscopically, the colored reaction product can be observed. The presence of the colored reaction product indicates that the target analyte was present, whereas no colored reaction product indicates that the target analyte was absent.

In a related staining method, IHC can be used (FIG. 1). First a tissue suspected of containing a target analyte is exposed to an antibody that has been produced to specifically bind with the target. In this case, the target is called an antigen, and it is most generally used to stain protein targets. The term immunohistochemistry technically refers to the staining of tissues using antibodies. However, for purposes of this disclosure isolated cells can also be stained.

As an example, an investigator may wish to analyze a tissue for the presence or absence of a particular protein. After the antibody is applied a binding event will occur if the target protein is present, but no binding will take place if the target protein is absent. The next step is to determine if a binding event has occurred. Prior to use, the antibody is labeled with a detectable marker. The detectable marker may be another antigen, small molecule, or enzyme. In one instance, the detectable marker is an enzyme. If the binding has occurred then the enzyme will be present at the binding site, otherwise no enzyme is present. Finally, the presence or absence of enzyme is determined, by application of a chromogen that reacts with the enzyme and is converted from a colorless chromogen to a colored chromogen that stains the area of the binding site.

Alternatively, instead of an enzyme, the probe or antibody could be labeled with another marker such as an antigen or small molecule. In fact, all antibodies contain within their native structures sequences of amino acids that are themselves antigens. Therefore, all antibodies inherently contain antigens that can be used as labels. In other embodiments, a small molecule can be synthetically incorporated into an antibody. Exemplary small molecules include fluorescein, biotin, or digoxigenin. These labels are not directly visualized, but are next linked by one or more intermediate steps to an enzyme. Such methods are called indirect methods. However, ultimately the binding site, through one or more intermediate steps, becomes labeled with an enzyme. One common example would be a first primary antibody of mouse origin, such as a monoclonal antibody, that binds to the target. Next, the secondary antibody containing an enzyme is applied. The secondary antibody may be, for example, an anti-mouse antibody, meaning that it can specifically recognize and bind to the native antigens within the primary antibody. The secondary antibody is an intermediate step which serves to link the enzyme to the primary antibody.

In addition, the enzyme may be chosen from any enzyme which is known to react with a colorless compound to create a colored chromogen capable of staining the tissue. The two most common enzymes for this purpose is Horseradish Peroxidase (HRP) and Alkaline Phosphatase (AP). Both HRP and AP have been used successfully in ISH and IHC procedures. Finally, multiple different chromogens are available for both enzymes that can yield multiple different colors.

Traditional Multiplex Staining

In certain instances, it is desirable to study two or more different analytes within a single tissue sample. In this method, a first analyte is stained a first color with a first chromogen using the methods of IHC or ISH described above. After the first analyte has been stained, the sample is stained a second time for a second analyte using a second chromogen to generate a second color that is distinct from the first color. In theory, this staining method can be repeated a number of times provided that each stain uses a unique chromogen that can be easily distinguished from the other chromogens. In practice, however, there are relatively few chromogens that are useful in multiplex staining. First, each chromogen must be useful in the IHC or ISH method. Second, each chromogen must generate a unique color. Third, each chromogen must not interfere with the color of the preceding chromogen(s). In multiplex staining, it is important that the different chromogens do not overlap each other as this overlapping produces undesirable colors that cannot be easily distinguished from the parent colors. For example, two chromogens commonly used in multiplex staining are DAB (brown), and Fast Red (red), and a third less commonly used chromogen is Fast Blue (blue). Thus, it is possible to stain three analytes as brown, red, or blue. It is not possible to overlap these chromogens to produce additional useful colors. DAB mixed with either of the other chromogens still produces brown. Fast Red and Fast Blue may produce intermediate colors between red and blue that are not easily distinguishable from either of the parent colors.

Methods of Chromogen Layering

The availability of multiple different colored chromogens is exploited in the disclosed and claimed methods of chromogen layering. A first chromogen layer is applied that stains the tissue a first color. Next a second chromogen is applied that stains the tissue a second color. By layering a second chromogen on top of a first chromogen, a third color is generated that is distinct from either of the first two colors. Thus, a useful and easy method to generate new color stains in a tissue has been discovered.

In traditional multiplex staining, described above, it is important that the chromogens do not overlap because this would produce undesirable colors that are not distinguishable from the parent colors. In contrast, with the disclosed claimed chromogen layering methods, the chromogens are purposely overlapped. In contrast to traditional multiplex staining, the claimed chromogen layering methods use a set of chromogens that have been specifically chosen to produce a desirable third color(s) when overlapped.

Analyses of Stained Biological Samples Using Chromogen Layering

The stained samples mounted on microscope slides are viewed under a microscope by a trained microscopist. The microscopist views the slides and notes the color pattern of staining. In certain areas of the slide where only one analyte is present, a single color will be observed. In other areas of the slide where at least two analytes are present, at least two different colors will be observed. A third color, if desired, can also be observed, specific for a third analyte. The claimed chromogen layering methods greatly increases the availability of different colors that can be observed, thereby increasing the number of analytes that can be studied.

The claimed chromogen layering method is similar to the multiplex method in that multiple analytes can be studied simultaneously. However, the chromogen layering method improves upon the multiplex method in several important aspects. First, there are new colors generated that were not previously available, thereby expanding the number of different colors available for evaluating analytes. Secondly, it is possible to stain three different analytes in a sample using only two different chromogens. A first analyte is stained with first chromogen, next a second analyte is stained with second chromogen, and next a third analyte is stained by overlapping the first and second chromogens. Whereas multiplex staining would require three different chromogens, chromogen layering can accomplish the same thing with only two chromogens.

In another embodiment, only one marker (for example, HRP) is used. HRP can react with a first substrate to produce a first chromogen layer, and then HRP can also react with a second substrate to produce a second chromogen layer. Therefore, it is possible to layer two chromogen layers using a single enzyme. A third color can result from the layering of the first and second chromogens.

As mentioned above, the stained microscope slides are observed under a microscope by a trained microscopist to determine whether a single analyte or multiple analytes are present in the sample based on the stain color and distribution. If a more precise measurement is desired, a digital image of the slide can be captured. The digital image is subjected to image analysis which analyzes the colored components of the digital image. For example, each pixel can be measured for red, green, and blue (RGB) values, or each pixel can be measured by another method for hue, saturation, and intensity. These measurements are then converted to quantitative values for each of the stained analytes.

EXAMPLES

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example 1: Chromogen Layering Triple Stain for Evaluation of Prostate Cancer

It is important to differentiate between benign and cancerous conditions of the prostate. Benign prostatic hyperplasia (BPH) is not cancer but may mimic cancer. Prostatic intraepithelial neoplasia (PIN) is an early-stage non-invasive neoplasm. Prostatic carcinoma is an invasive cancer. The treatment for these three disease states is quite different so accurate diagnosis is essential. Immunohistochemistry may be used for this purpose. In this method, a nuclear marker for basal epithelial cells, such as P63 is selected as the first analyte. A second analyte, also to basal epithelial cells is cytokeratin, which stains the cell's cytoplasm, and a third analyte, AMACR, is selected which stains the cytoplasm of prostate cancer cells. The evaluation of these three stains can be used to differentiate between the three prostate diseases listed above. A stain showing only the first two analytes (basal epithelium) can rule out PIN and prostate carcinoma. A stain showing prostate cancer cells (analyte 3) totally circumscribed by basal epithelium (analytes 1 and 2) can rule out invasive cancer and is indicative prostatic intraepithelial neoplasia. A stain showing prostate cancer cells without basal epithelium, or a fragmented basal epithelial layer, is indicative of invasive cancer.

In this method, a tissue biopsy is obtained from a patient suspected of having a prostate carcinoma. The biopsy is prepared for examination by fixation, embedding, sectioning, deparaffinization, rehydration, and target retrieval.

Figure 2:
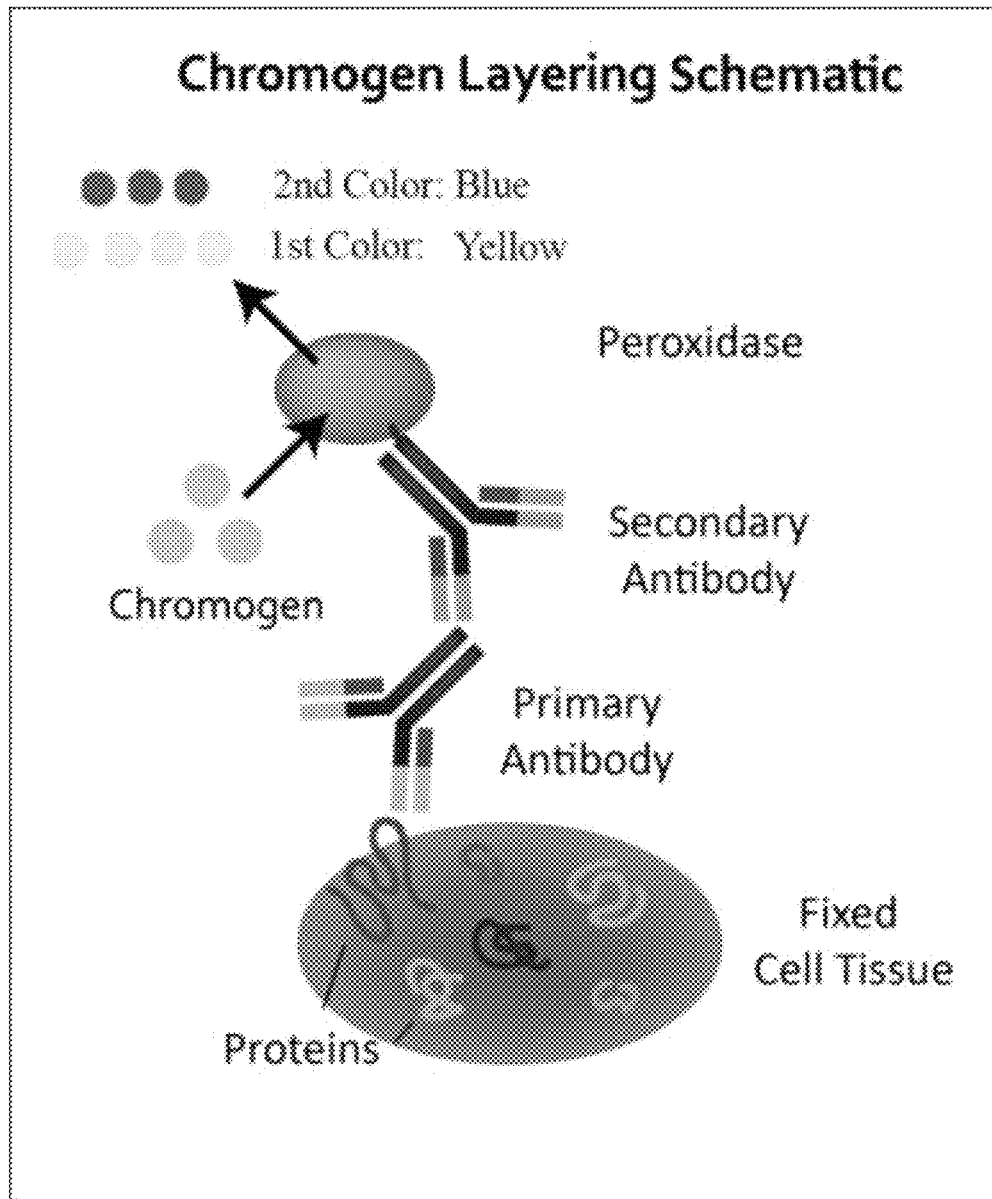
FIG. 2 shows a diagram illustrating the chromogen layering method of the present disclosure: 1) primary antibody, 2) secondary antibody containing 3) an enzyme (peroxidase or alkaline phosphatase, and 4) two colored layers, a first colored layer of yellow, and a second colored layer of blue.

The slides thus prepared are stained by the IHC method according to the following protocol. See FIG. 2 for an overview of the following procedure.

1. Incubate slides with a cocktail of antibodies to P63 (analyte 1, basal epithelial nuclei) and cytokeratin (analyte 2, basal epithelial cytoplasm) for 20 minutes, rinse.
2. Incubate slides with linker antibody labeled with HRP for 20 minutes, rinse.
3. Incubate slides with a first chromogen of PermaYellow/HRP to generate a yellow stain for P63 (analyte 1) and cytokeratin (analyte 2).
4. Incubate slides with a second cocktail of antibodies to cytokeratin (analyte 2, basal epithelial cytoplasm) and AMACR (analyte 3, prostate cancer cells cytoplasm) for 20 minutes, rinse.
5. Incubate slides with linker antibody labeled with HRP for 20 minutes, rinse.
6. Incubate slides with a second chromogen, HRP-Blue for five minutes to generate a second color of blue for cytokeratin (analyte 2) and AMACR (analyte 3). Because cytokeratin (analyte 2) was previously yellow from the first chromogen, the second chromogen of HRP-Blue overlays the yellow color to produce a third color of green.
5. Examine slides for the presence of yellow color (nucleus of basal epithelium), green color (cytoplasm of basal epithelium), and blue color (prostate cancer cells).

Example 2: Primary Chromogen Colors

Figure 3:
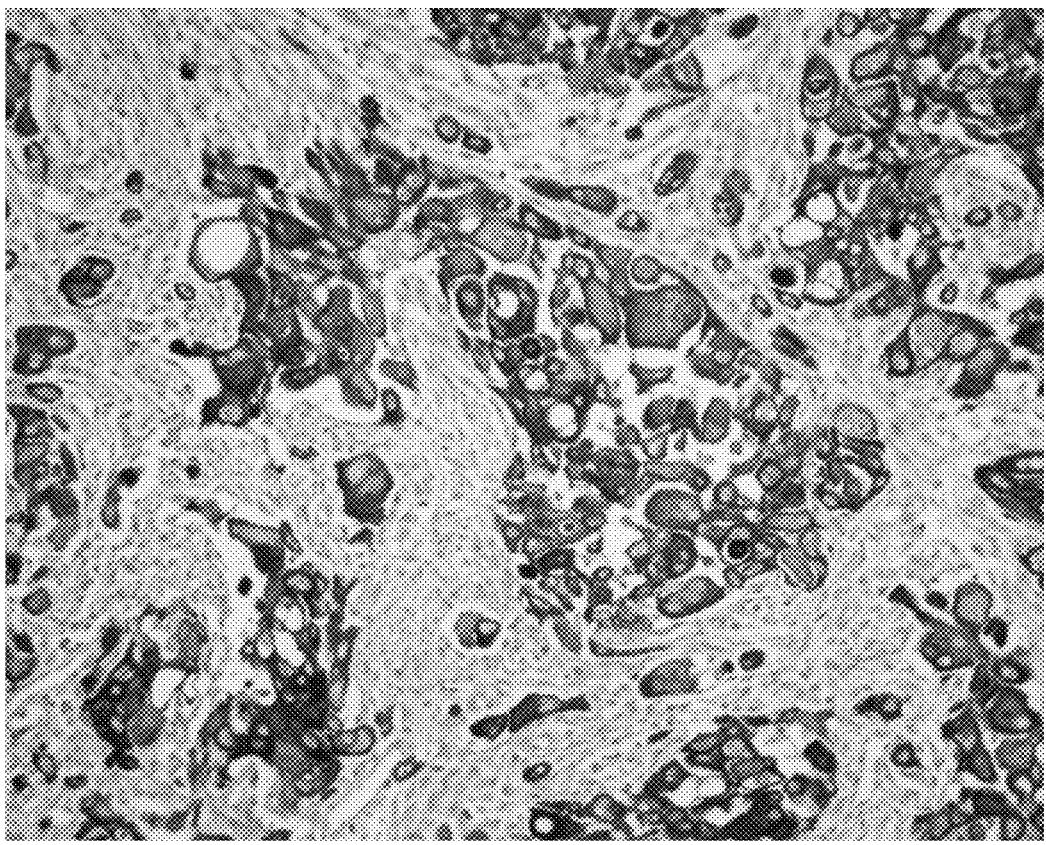
FIG. 3 to FIG. 6 show original colors of the chromogens used in the disclosed methods.

FIG. 3 shows a breast cancer tissue stained with a Her2/neu antibody. The chromogen used was Stable DAB Plus. The primary chromogen color is brown.

Figure 4:
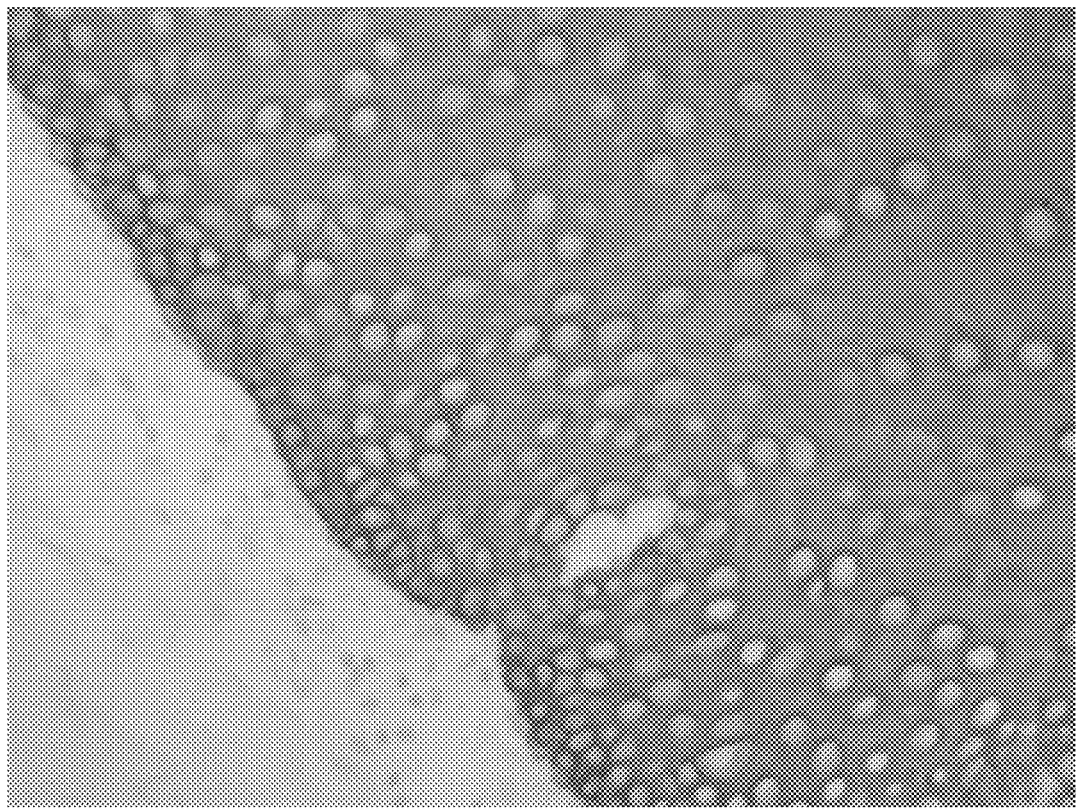

FIG. 4 shows a tissue sample obtained from a tonsil stained with an antibody directed to HMW Cytokeratin. The chromogen used was PermaYellow/HRP. The primary chromogen color is yellow.

Figure 5:
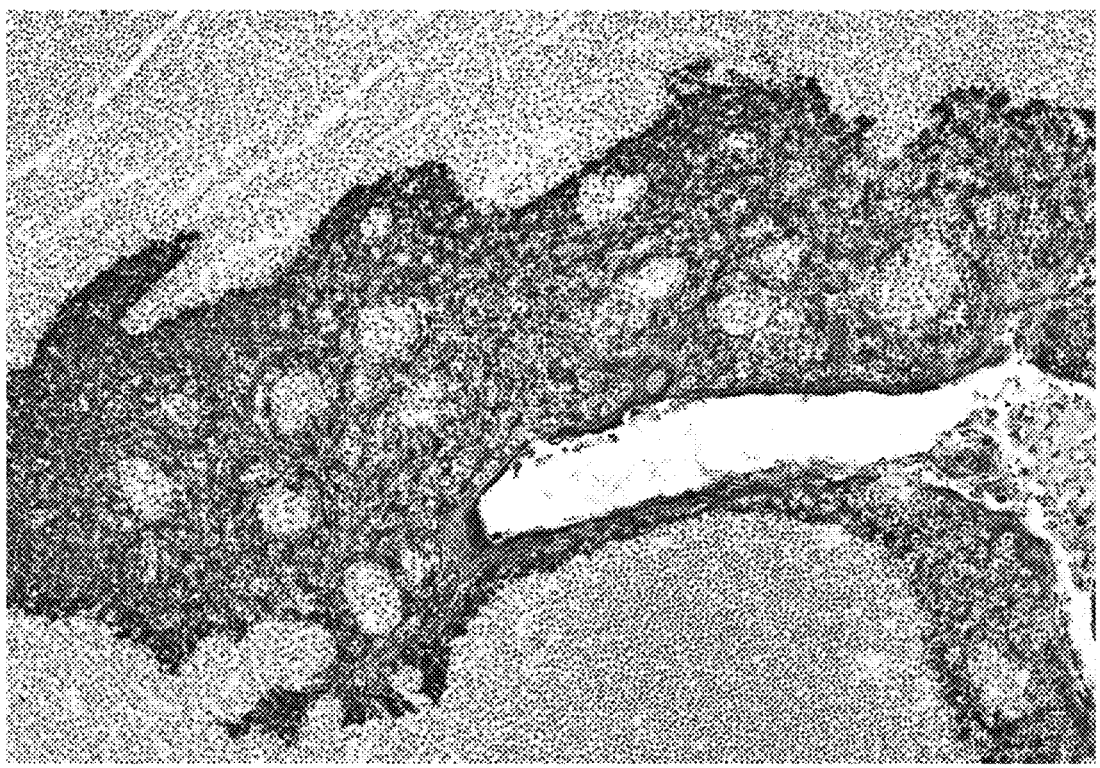

FIG. 5 shows a tissue sample obtained from a tonsil stained with an antibody directed to HMW Cytokeratin. The chromogen used was PermaRed/HRP. The primary chromogen color is red.

Figure 6:
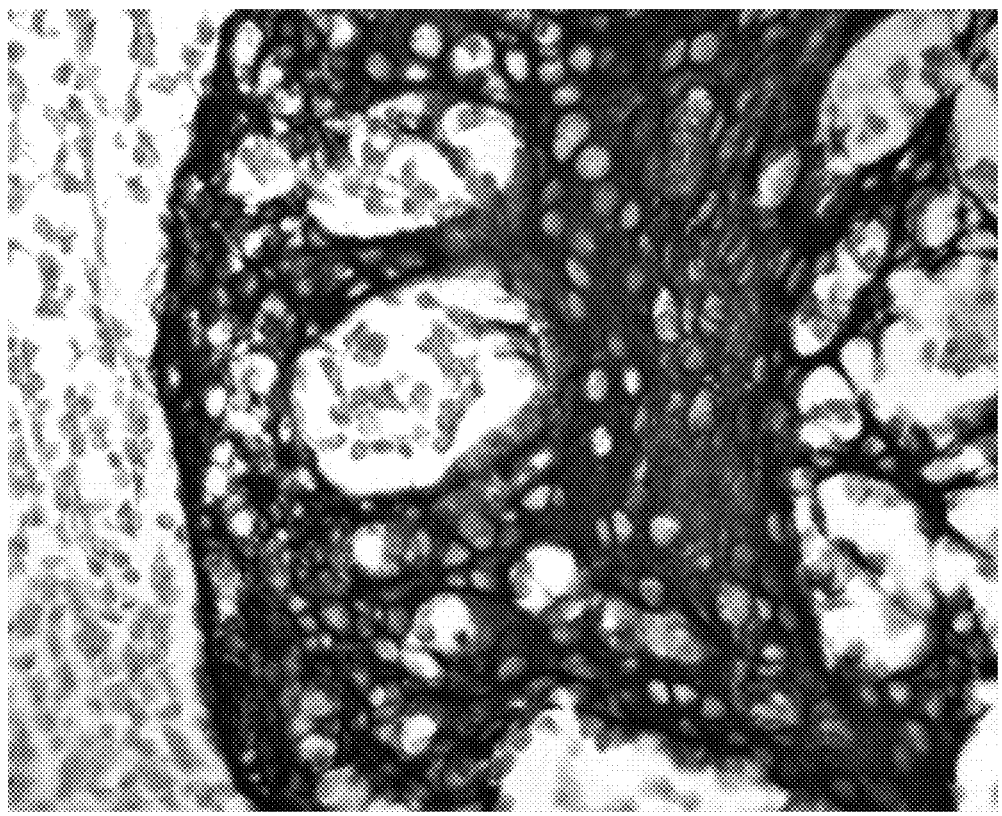

FIG. 6 shows a tissue sample obtained from a tonsil stained with an antibody directed to HMW Cytokeratin. The chromogen used was PermaBlue/HRP. The primary chromogen color is blue.

Example 3: Chromogen Layering

The experiments described below show that by layering some of the disclosed chromogens, a useful third color was not produced. In some experiments, the final color remained essentially the same (FIG. 7 and FIG. 8) mainly brown. These two experiments show that not all chromogen combinations produce useful third colors. Specifically, chromogens based on DAB, such as Stable DAB Plus are the most commonly used chromogens for IHC, but DAB cannot be used for chromogen layering. Only certain color combinations are useful, as shown below in FIG. 9 to FIG. 12.

Figure 7:
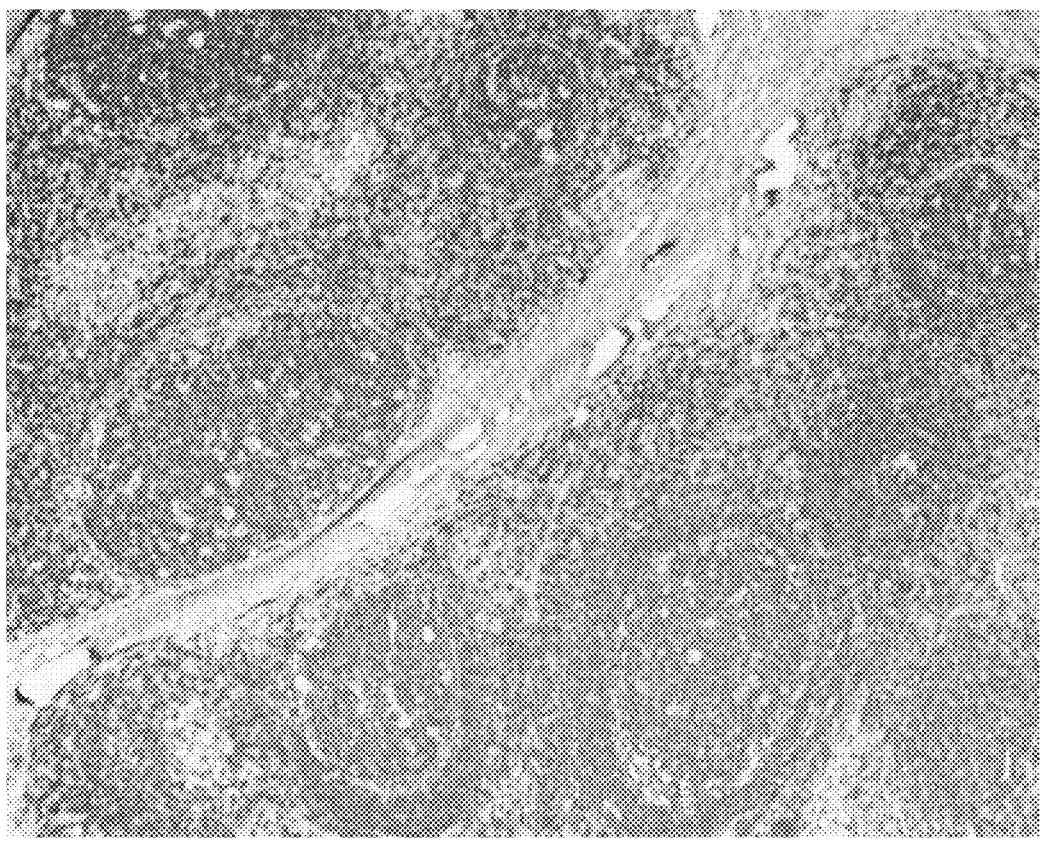
FIG. 7 to FIG. 12 show chromogen layering using the disclosed methods.

FIG. 7 shows a tissue sample obtained from a tonsil stained with an antibody directed to CD20. The first chromogen used was Stable DAB Plus and the second chromogen used was PermaYellow/HRP resulting in an overlapping color of brown that was not useful for analysis.

Figure 8:
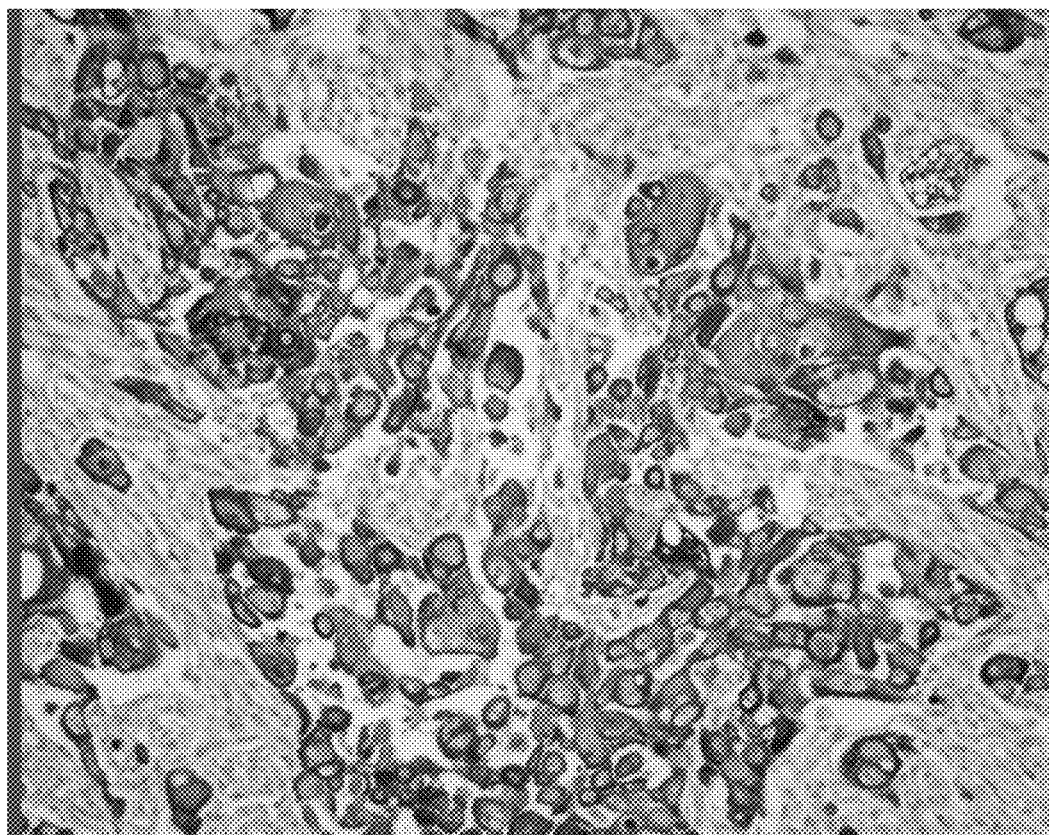

FIG. 8 shows a breast cancer tissue stained with a Her2/neu antibody. The first chromogen used was Stable DAB Plus and the second chromogen used was PermaRed/HRP resulting in an overlapping color of brown that was not useful for analysis.

Figure 9:
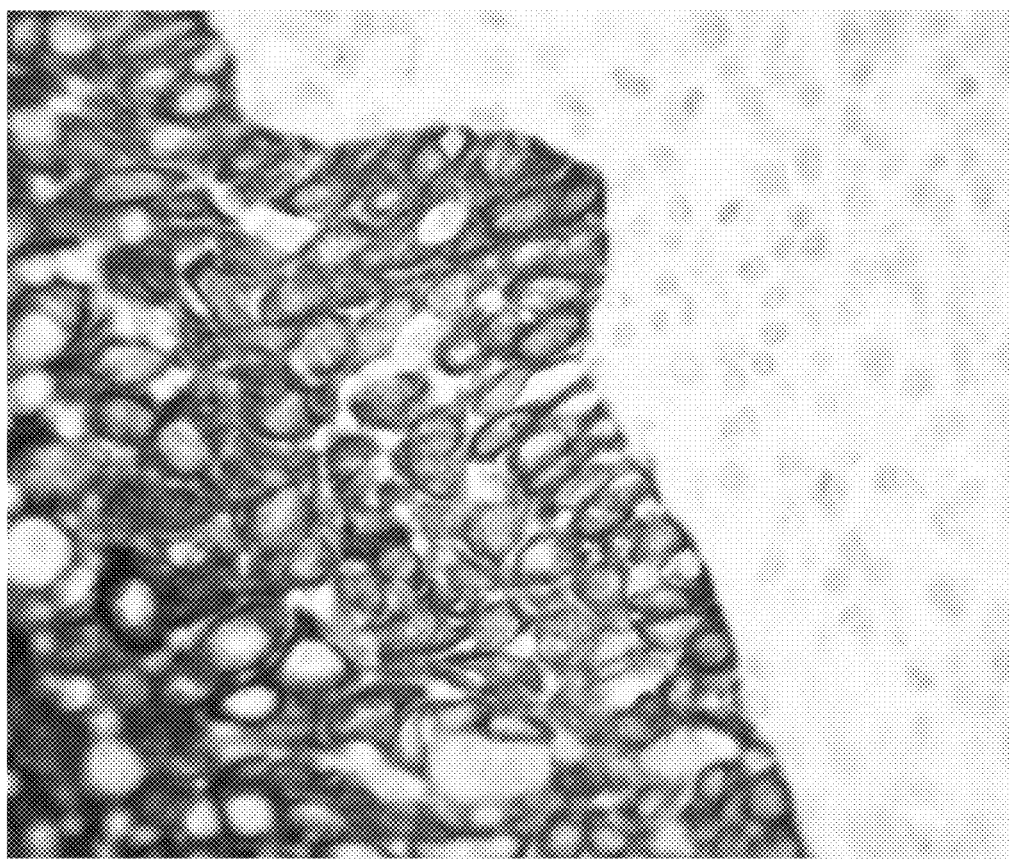

FIG. 9 shows a tissue sample obtained from a tonsil stained with an antibody directed to HMW Cytokeratin. The first chromogen used was HRP Blue and the second chromogen used was PermaYellow/HRP resulting in an overlapping color of green that was useful for analysis.

Figure 10:
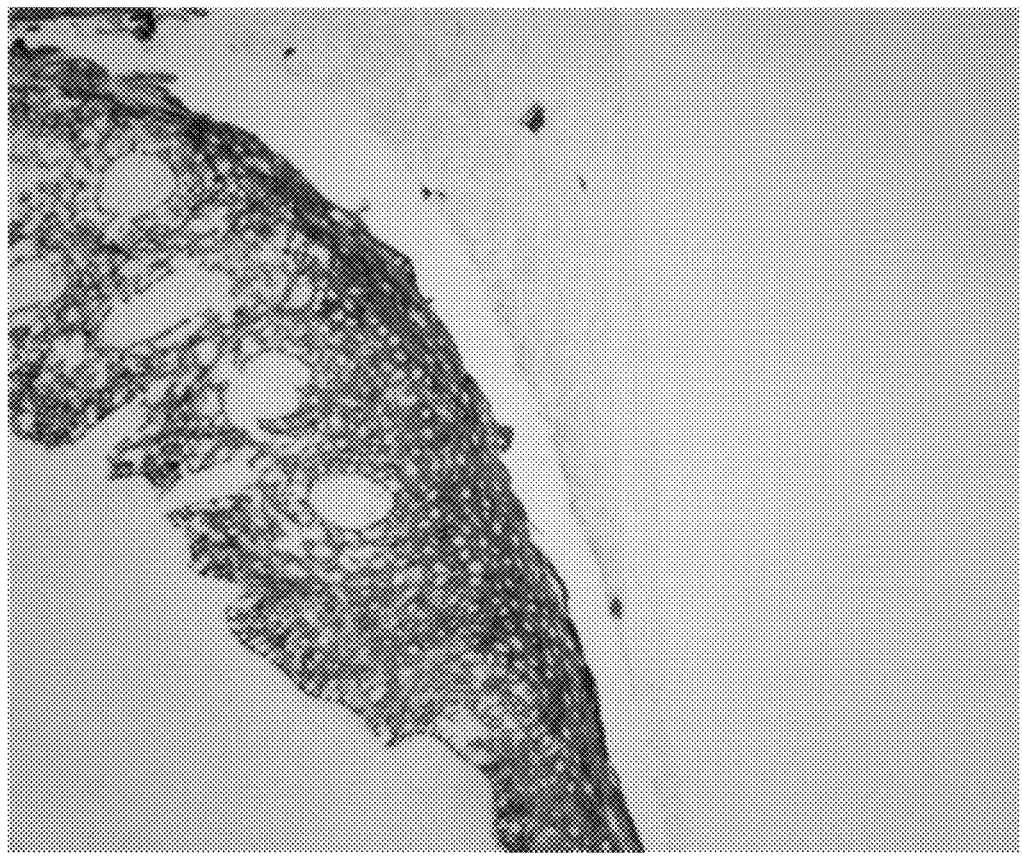

FIG. 10 shows a tissue sample obtained from a tonsil stained with an antibody directed to HMW Cytokeratin. The first chromogen used was HRP Blue and the second chromogen used was PermaRed/HRP resulting in an overlapping color of purple that was useful for analysis.

Figure 11:

FIG. 11 shows a tissue sample obtained from a tonsil stained with an antibody directed to HMW Cytokeratin. The first chromogen used was PermaYellow/HRP and the second chromogen used was PermaRed/HRP resulting in an overlapping color of orange that was useful for analysis.

Figure 12:
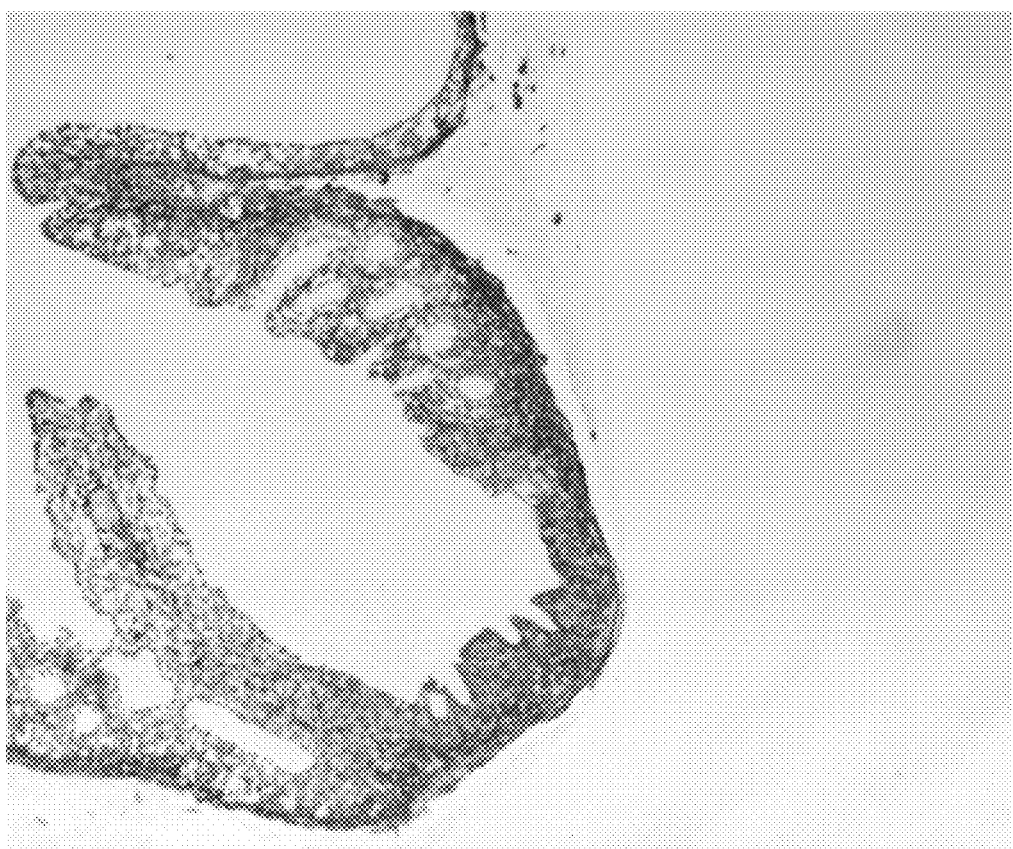

FIG. 12 shows a tissue sample obtained from a tonsil stained with an antibody directed to HMW Cytokeratin. The first chromogen used was AP-Red and the second chromogen used was PermaBlue/HRP resulting in an overlapping color of purple that was useful for analysis.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of staining a biological specimen for a first analyte, the method comprising:
   obtaining a section of a biological specimen;
   contacting the section with a first antibody directed towards the first analyte, wherein the first antibody is labeled with a first marker or wherein the first antibody becomes labeled with a first marker by means of a linking step;
   contacting the section with a first chromogen that reacts with the first marker to generate a first color;
   contacting the section with a second chromogen that reacts with the first marker directed to the first analyte to generate a second color which overlays the first color creating a third color; and
   visually observing the presence or absence of the first, the second, or the third color wherein the third color is created by overlaying the first and the second colors onto the first marker targeted to the first analyte.

2. The method of claim 1, wherein the first chromogen comprises one of; 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, and naphthol-blue, and the second chromogen comprises one of; 3, 3'-diaminobenzidine, 3, 3', 5, 5'tetramethylbenzine, HRP-Red, HRP-Blue, HRP-Yellow, PermaYellow/HRP, Fast Red/Naphthol Phosphate, PermaRed/HRP, naphthol-red, Fast Blue/Naphthol Phosphate, PermaBlue/HRP, and naphthol-blue.

3. The method of claim 1, wherein:
   a) the first chromogen's color is blue, the second chromogen's color is yellow, and the third color is green; or
   b) the first chromogen's color is yellow, the second chromogen's color is blue, and the third color is green; or
   c) the first chromogen's color is blue, the second chromogen's color is red, and the third color is purple; or
   d) the first chromogen's color is red, the second chromogen's color is blue, and the third color is purple; or
   e) the first chromogen's color is yellow, the second chromogen's color is red, and the third color is orange; or
   f) the first chromogen's color is red, the second chromogen's color is yellow, and the third color is orange.

4. The method of claim 1, wherein the first marker is an enzyme.

5. The method of claim 4, wherein:
   the enzyme is selected from one of a: peroxidase, horse radish peroxidase, a phosphatase, alkaline phosphatase, and beta-galactosidase.

6. The method of claim 1, wherein the biological specimen is observed using light microscopy to determine the presence of one of; the first color, the second color, and the third color.

7. The method of claim 1, wherein the first marker is a peroxidase enzyme.

8. The method of claim 7, wherein the peroxidase enzyme reacts with both the first chromogen and the second chromogen while bound to the first analyte.

9. The method of claim 8, wherein the first chromogen and the second chromogen each comprise at least one of: 3, 3'-diaminobenzidine, 3, 3', 5, 5'tetramethylbenzine, HRP-Red, HRP-Blue, HRP-Yellow, PermaYellow/HRP, PermaRed/HRP, PermaBlue/HRP.

* * * * *